United States Patent
Carlson et al.

(10) Patent No.: US 6,718,197 B1
(45) Date of Patent: Apr. 6, 2004

(54) LV ECTOPIC DENSITY TRENDING

(75) Inventors: Gerrard M. Carlson, Champlin, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 637 days.

(21) Appl. No.: 09/704,844

(22) Filed: Nov. 2, 2000

(51) Int. Cl.[7] ............................................... A61B 5/04
(52) U.S. Cl. ........................................ 600/515; 607/32
(58) Field of Search ........................... 600/516, 519, 600/521, 515; 128/903; 607/30–32, 60

(56) References Cited

U.S. PATENT DOCUMENTS

| | | | |
|---|---|---|---|
| 4,566,461 A | 1/1986 | Lubell et al. | 128/668 |
| 4,796,620 A | * 1/1989 | Imran | 600/519 |
| 5,291,400 A | 3/1994 | Gilham | 364/413.06 |
| 5,411,031 A | 5/1995 | Yomtov | 128/706 |
| 5,448,998 A | 9/1995 | Ito et al. | 128/718 |
| 5,603,331 A | * 2/1997 | Heemels et al. | 600/508 |
| 5,899,931 A | * 5/1999 | Deschamp et al. | 607/60 |
| 6,026,320 A | 2/2000 | Carlson et al. | 600/510 |

* cited by examiner

*Primary Examiner*—Mark Bockelman
(74) *Attorney, Agent, or Firm*—Thomas J. Nikolai; Nikolai & Mersereau, P.A.

(57) ABSTRACT

Ectopic beat activity detection of the human heart is monitored by time interval measurements of depolarizations in the heart. The intervals between beats are categorized as being long beats, short beats or normal beats. Then the sequence of categories of beats is analyzed to determine the types of ectopic beats occurring and to count such occurrences and display such information to a health care provider to help monitor, diagnose and treat patients. For patients with pacemakers installed the information can be used to adjust pacemaker settings. The information may also be used to alert the health care providers to dangerous patterns indicating serious conditions which need immediate treatment.

14 Claims, 7 Drawing Sheets

NORMAL HEART

DISEASED HEART

LV ECTOPIC DENSITY TRENDING

BACKGROUND OF THE INVENTION

1. Field of the Invention

This invention relates generally to the cardiac rhythm monitoring. More particularly, the invention relates to detection, classification, and display of ectopic beat patterns by their statistical indices and time domain signatures.

2. Description of the Related Art

Physicians typically detect ectopic beats by visually analyzing electrocardiograms (ECGs). To detect the beats, the physician analyzes changes in waveform morphology from the ECG tracings. The ECG tracings provide the physician with a large amount of data to examine while looking for the ectopic beats. In addition, the examination generally requires a patient to visit a physician's office and be hooked up to an ECG recording device. Although this procedure identifies ectopic beats during the office visit, the procedure does not reveal the history of ectopic beats that would help to better assess the patient's overall well being. Alternatively, the patient may transmit ECG data to the physician using a telephone line. Unfortunately, telephonic transmission of heart rate rhythms typically does not include all of the data from the ECG recording due to limitations on telephonic transmission of the data. Therefore, this method is not as accurate as an office visit.

Due to the large amounts of data needed to record waveforms for a physician to observe morphology related ectopic beats, the ECG's used are usually not from implantable devices which typically have limited data memory. Therefore, implantable devices can only provide short snapshots of the morphology data needed to detect ectopic beats.

Hence, there is a need to provide an implantable device for monitoring ectopic beats long term for assessing patient well being and providing the physician with useful trending data for diagnosing and treating a patient.

SUMMARY OF THE INVENTION

The present invention provides a method of detecting ectopic beats requiring less memory than a full ECG tracing. The reduced memory requirement permits the methods use in conjunction with implantable medical devices such as pacemakers.

By limiting analysis of ectopic rhythms to strictly interval sequences of interval profiles, a longer record of the patient's ectopic heart activity based solely on the intervals themselves can be stored. One of the benefits of using the intervals is that it requires less memory. Another benefit is that the characterization methods are different and because it requires less memory to get representation of the ectopic beats an implantable device is possible.

A normal R to R interval is established by looking at the median of R to R intervals for a period of time. A threshold can then be established as a percentage above and below the median of the R to R interval. These upper and lower thresholds are used to determine whether or not an event is ectopic.

After having determined an event is ectopic, a microprocessor assigns a value of normal (n), short (s), or long (l) to the R to R interval and stores the sequence of determinations (i.e., n, n, n, s, l, s, l) that characterizes the event sequence. The R to R interval's values (i.e., n, s or l) form patterns. The stored patterns are used as a dictionary for classifying the ectopic event types. The event types are identified by the microprocessors which then counts and reports events over an extended period of time. The microprocessor may also be programmed to change pacing therapy.

A transmitter connected to the microprocessor can then report the data collected by telemetry to a receiver. The receiver can then transfer the data to a device which converts the data into graphical form for presentation to a physician for analysis.

OBJECTS OF THE INVENTION

It is an object of the invention to use interval information only to detect and categorize the ectopic activity in a heart.

It is an object of the invention to reduce the amount of memory needed in an implantable device to provide ectopic beat information to a health care provider.

It is an object of the invention to implant a medical device in a patient for detecting and categorizing ectopic activity in the heart.

It is an object of the invention to categorize ectopic events through the use of sequences of declared normal, short and long categorizations and to trend the frequency of the total number of occurrences of ectopic beats.

It is an object of the invention to use a state transition table to assist in the identification of event types.

It is an object of the invention to track ectopic events by day, week or other time period.

It is an object of the invention to track ectopic events by their category.

It is an object of the invention to plot or graph ectopic activity as a function of heart rate over twenty-four hour period or other periods of time.

It is an object of the invention to provide a two-dimensional histogram versus interval or heart rate to display the ectopic beat data.

It is an object of the invention to telemeter the ectopic beat information from the implanted device to a receiver.

It is an object of the invention to change the pacing of the heart based on the ectopic beat information detected.

It is an object of the invention to provide information useful in assessing patient well being and for adjusting patient therapy.

Other objects, advantages and novel features of the present invention will become apparent from the following detailed description of the invention when considered in conjunction with the accompanying drawing.

DETAILED DESCRIPTION OF THE INVENTION

Figure 1:
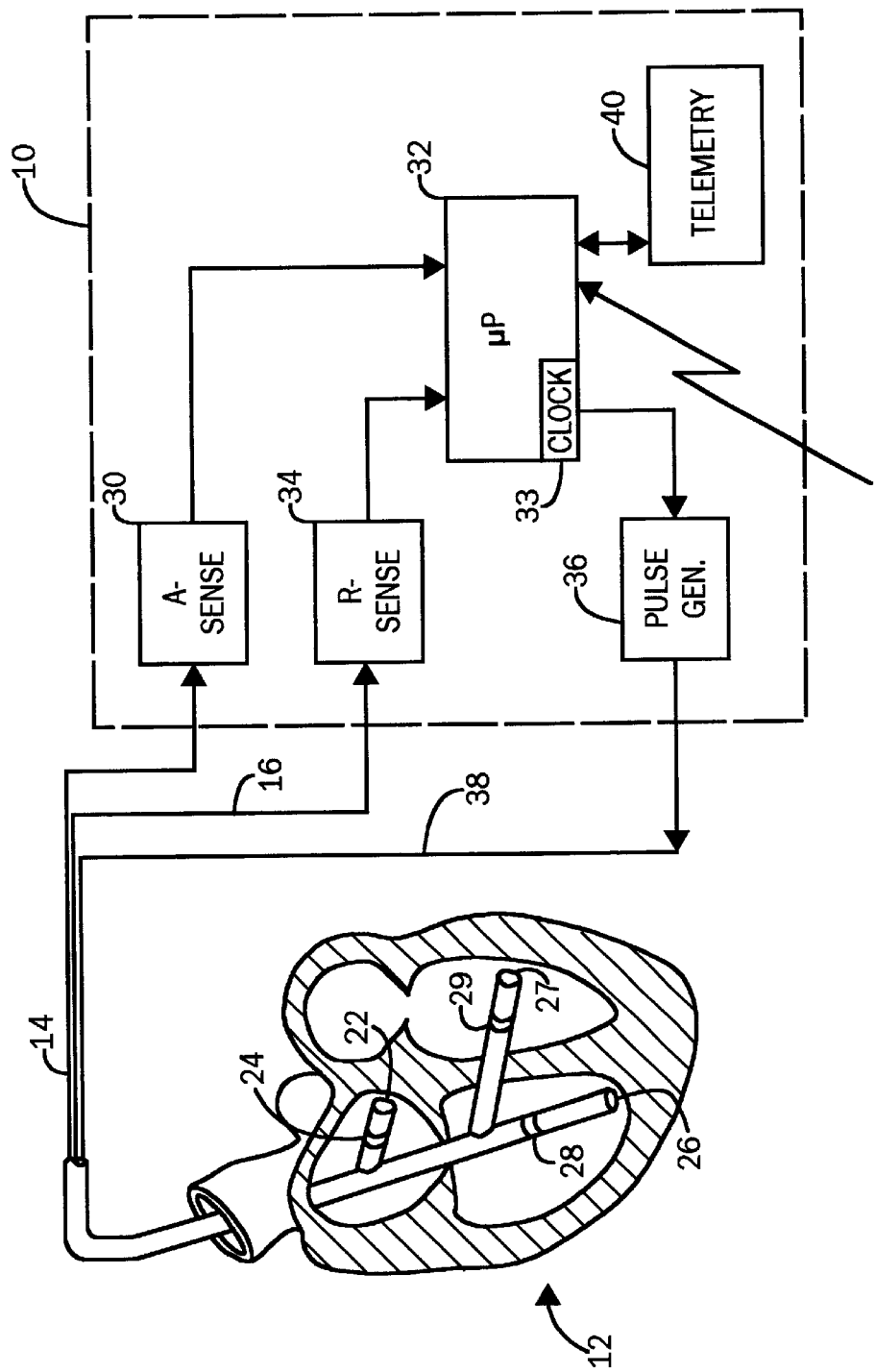
FIG. 1 shows an implantable microprocessor having sensors and leads connected to a heart.

FIG. 1 shows a human heart 12 with an atrial lead 14 having sensors 22 and 24 for detecting electrical activity such as heart muscle depolarization. Also shown is ventricular lead 16 having sensors 26, 28 for the right ventricle and sensors 27, 29 for the left ventricle. The atrial lead 14 provides a path for electrical signals from the heart 12 to an atrial signal sensor and amplifier 30 inside pacing device 10. Similarly, ventricular lead 16 provides a path for electrical signals from the heart 12 to a ventricular signal sensor and amplifier 34 inside pacing device 10. A microprocessor 32 receives the signals from the atrial amplifier 30 and the ventricular amplifier 34 to process the signals for detecting ectopic beats. The microprocessor 32 has a clock 33 for measuring the time between detected depolarizations from the sensors in the heart 12. The microprocessor 32 has a memory for storing the data received and for storing software needed to process the data received. The microprocessor 32 can provide instructions to a pulse generator 36 to provide a pulse of electricity which will travel through lead 38 to stimulate the heart 12. FIG. 1 also shows the microprocessor 32 connected to a telemetry device 40 for transmitting data from the pacemaker 10 and for receiving instructions for the pacemaker.

Figure 2:
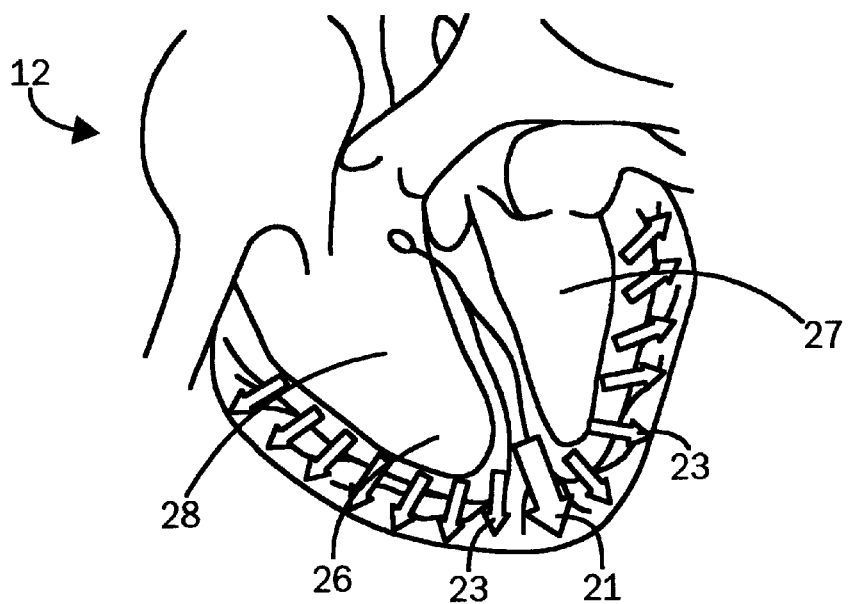
FIG. 2 shows a heart having a normal depolarization pattern.
Figure 3:
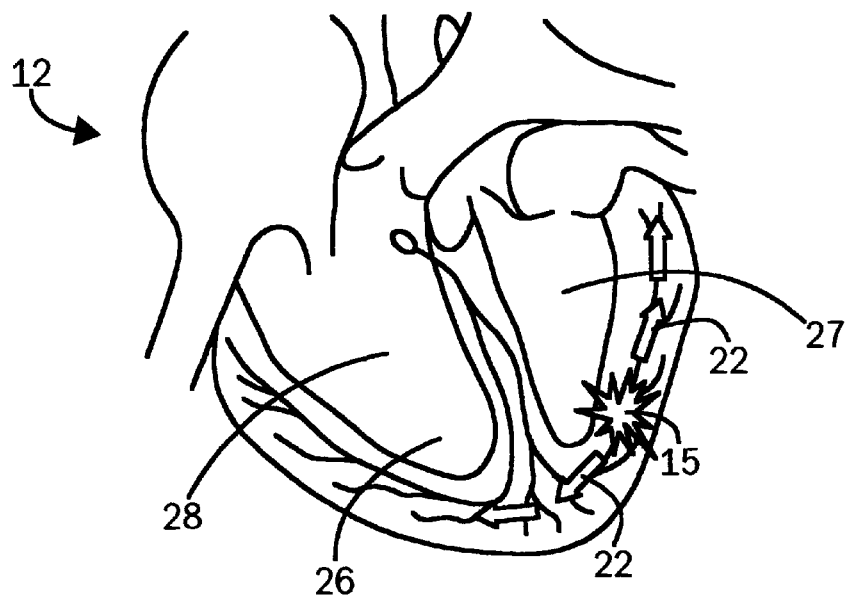
FIG. 3 shows a heart wherein an ectopic focus has originated the contraction and the ventricle has an abnormal depolarization sequence.

FIGS. 2 and 3 illustrate examples depolarization patterns for normal and ectopic beats, respectively. FIG. 2 shows a myocardial depolarization of heart 12 during a normal heartbeat. The large vector arrows 21 show the origin of the beat and the smaller vector arrows 23 show the propagation through the myocardium from the origin. Alternatively, the origin of the beat may originate from an ectopic focus in some patients. FIG. 3 shows an example of a myocardial depolarization of heart 12 where an ectopic focus 15 generates the heartbeat. The vector arrows 22 show the propagation from an ectopic focus 15.

Figure 4:
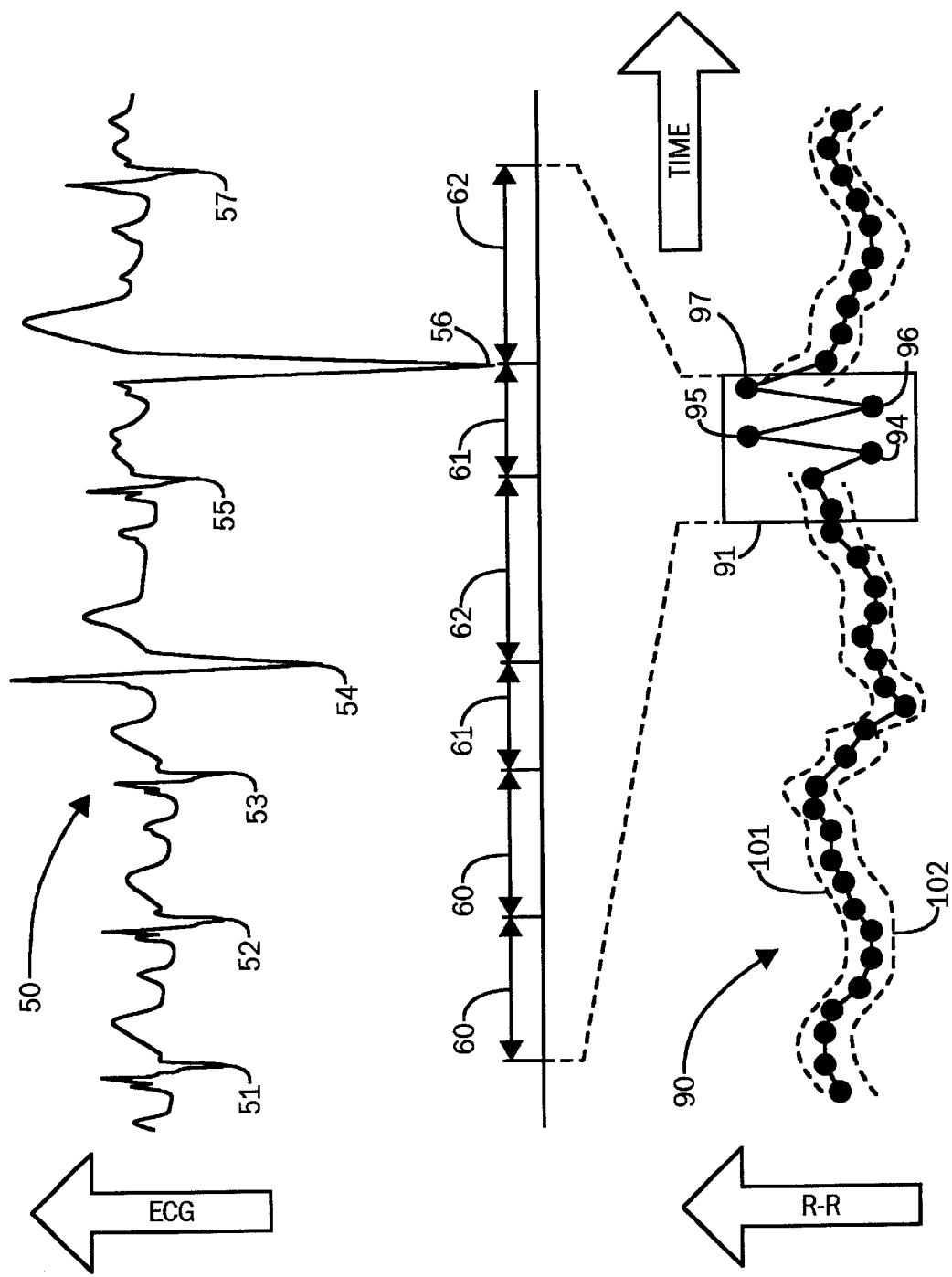
FIG. 4 shows an exemplary electrocardiogram signal, the corresponding R to R and R to ectopic interval sequence, and the trending curve for the interval sequence.

FIG. 4 shows an ECG waveform 50 which could be derived from a surface ECG or an endocardial signal. When derived from an endocardial signal the waveform would typically be derived from one or more signals sensed in the ventricles and/or atria of the patient's heart. ECG waveform 50 includes normal amplitude R-waves 51, 52, 53, 55 and 57. The R-waves 54 and 56 have anomalous amplitudes and are representative of ectopic heartbeats. Normal heartbeats typical yield regular intervals between R-waves as illustrated by time interval 60. The time intervals are typically measured between R to R peaks. The intervals 60, 61 and 63 correspond to the ECG trace 50 and show a sequence of time intervals between detected ventricular depolarizations 51 through 57. The time intervals between beats 51 and 52, and 52 and 53 are indicative of a normal time interval 60 (n) between beats. An ectopic focus generates a change in the morphology of the R-wave and a change in the time interval between them. Beat 54 is an ectopic beat that may represent a PVC. Beat 54 accounts for the shortened time interval 61 (s) between peaks 53 and 54. Shortened interval 61 (s) is followed by a compensatory pause 62 (L) between peaks 54 and 55. Compensatory pause 62 (L) is generally a lengthened time interval until the following beat. The following heartbeat 55 is a normal heartbeat. Again, an ectopic beat 56 accounts for a second shortened time interval 61 (s) between peaks 55 and 56 and a compensatory pause 62 (L) between ectopic beat 56 and normal beat 57. A normal time period 60 (n) is resumed between peak 56 and subsequent beats as indicated by the trending of R to R intervals 90 below the ECG trace.

Region 91 of trending curve corresponds to ECG trace 50. Trending curve 90 shows the sequence of detected R to R intervals on a larger scale than ECG trace 50. Each point plotted on trending curb 90 represents a time interval between consecutive R-waves. The actual points plotted on trending curve 90, except for points 94–97, are very close to a median value of the R to R interval times based on N/2 measurements. The N/2 measurements are typically made before and after the current interval time plotted. The normal trend lines 101 and 102 for the high and low normal figures, respectively, are calculated as a percentage of or a difference from a non-ectopic sinus interval estimate or other ordered statistic filter, such as a moving window median. Those skilled in the art will recognize that a variety of additional methods may be used to estimate what the time interval would have been if the beat was not an ectopic beat. Region 91 shows a sequence of abrupt changes from trending curve 90, where the intervals are much shorter and much longer for a brief period of time.

The designators of n for normal, s for short and L for long are assigned to the time intervals between depolarizations based on whether the point falls between, below or above the normal trending lines 101 and 102, respectively. As shown in FIG. 4, trending line 90 data points 94, 95, 96, 97 are outside the normal range, points 94 and 96 being below the range and points 95 and 97 being above the range. Thus, the series of beats for region 91 in terms of interval lengths is n, n, s, L, s, L.

Figure 5:
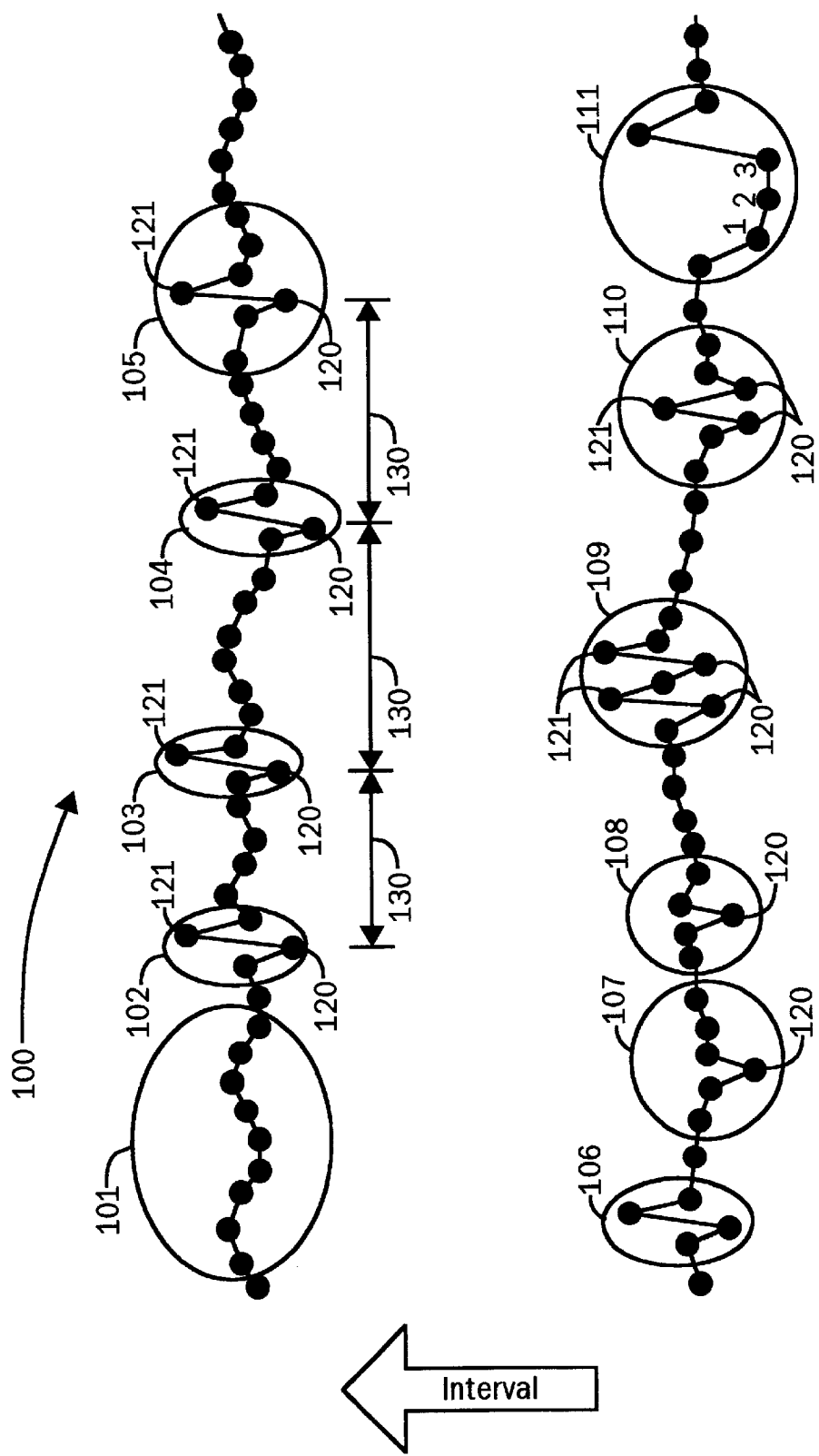
FIG. 5 shows an example of a trending curve illustrating various signatures of ectopic activity.

In FIG. 5, trending curve 100 illustrates a sequence of normal R to R intervals, exemplified by circled region 101, followed by a sequence of abrupt departures from the interval shown in circled regions 102, 103, 104 and 105. These abrupt departures represent ectopic beats. Each circled region 102 through 105 includes a short interval 120 followed by a long interval 121. The time between the ectopic beats are the ectopic to ectopic intervals 130. Ectopic intervals 130 are important to note because the intervals reveal information about the patient's condition.

Highlighted area 106 shows another PVC with a long interval 121, similar to those in 102 through 105. However, the ectopic beat in region 106 is followed by an interpolated PVC ectopic beat in region 107 and a second interpolated PVC ectopic beat in region 108. The interpolated PVC ectopic beats show a departure from normal rhythms where trending in curve 100 includes a short interval 120 mixed in with a number normal intervals. Regions 109 and 110 show other types of abnormal cardiac rhythms characterized by short interval 120—long interval 121 sequences. In addition, region 111 shows a run of three PVC having a pattern of n, s, s, s, L, n, which can be a precursor to a malignant cardiac rhythm, such as a ventricular fibrillation. This pattern identifies a rhythm to be regarded as very serious, and is an indicator that an appropriate treatment should be initiated.

Microprocessor 32 is programmed to identify and classify the various patterns of n, s, and L intervals. Microprocessor 32 may identify and classify patterns using various methods. Generally, microprocessor 32 looks at the sequences of normal, long, and short, intervals to identify certain rhythm types as being more lethal or serious than others. Multiple PVCs followed by limited normal activity represent an example of a more lethal rhythm.

Figure 6:
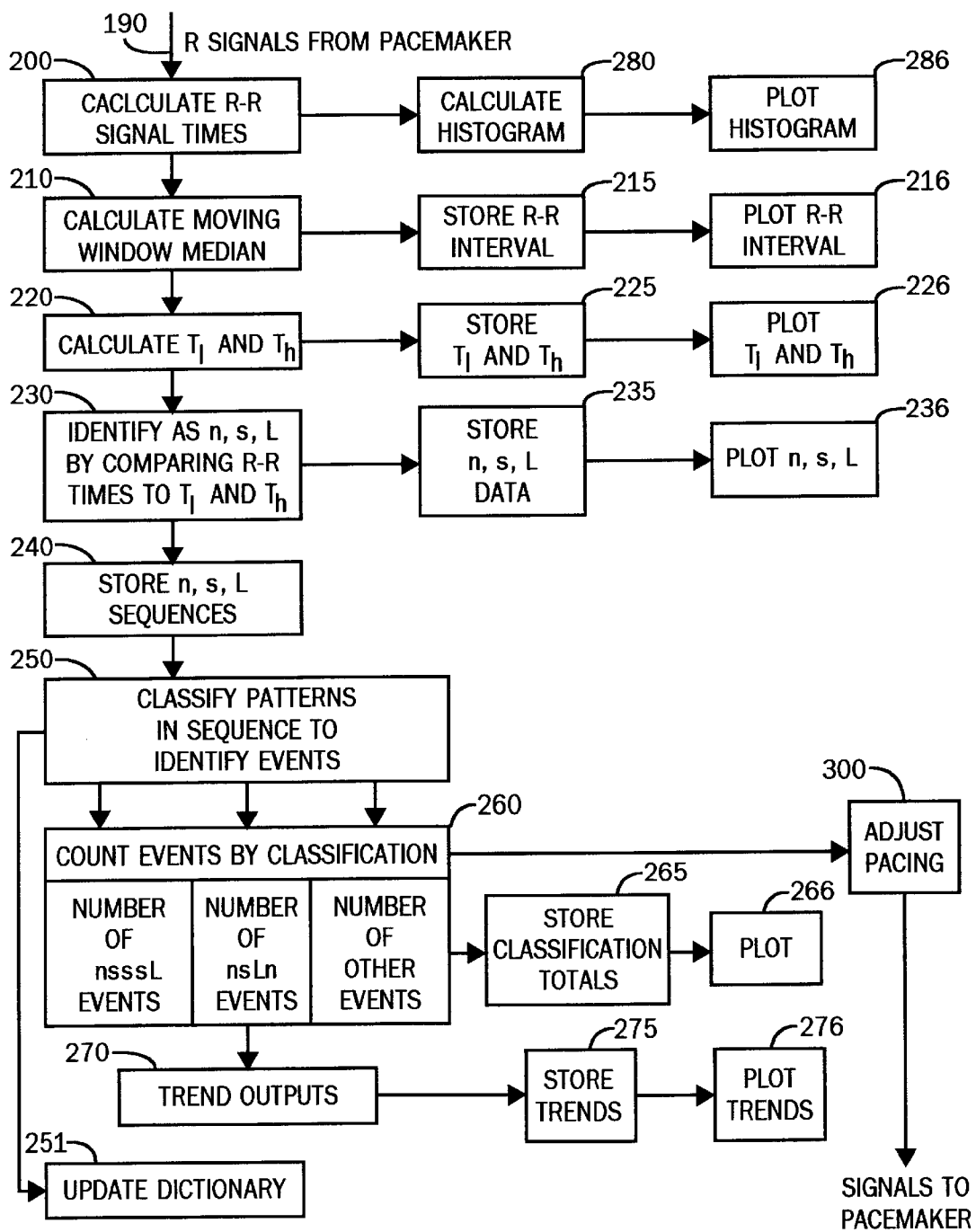
FIG. 6 is a flow chart illustrating an algorithm used by the microprocessor to find intervals containing information for identifying ectopic intervals and classifying the ectopic intervals into types of ectopic beats for counting and display.

FIG. 6 shows an exemplary flow diagram of an algorithm for calculating the n, s, and L time intervals and recognizing ectopic beat patterns. The beats may then be tabulated and displayed. With this algorithm implemented in the software to be executed by the microprocessor 32, this hardware/software combination comprises a means for processing time intervals between detected depolarizations such that ectopic activity can be detected and classified. As shown, depolarization signals 190 from the patient are used by the microprocessor in the algorithm. The R to R interval is calculated in a step 200. After N intervals are collected, a moving median window, for example, over a sequence of N intervals may be calculated in a step 210. The N intervals typically include a half-look ahead and a half-look behind. Thus, the classification or the detection of the ectopic interval is done N/2 using information N/2 ahead and N/2 behind the currently considered beat. The Median R to R intervals are then stored as step 215 and can be plotted in a step 216.

Thresholds, above ($T_h$) and below ($T_l$), the median interval are then established in a step 220 to differentiate between s, n, and L intervals. The difference between the thresholds and the median value will vary depending on the particular definition being use for ectopic beat. To calculate the $T_h$, the current median value from 210 is multiplied a value greater than 1.0. The $T_h$ value can then be stored in a step 225 and plotted in a step 226. Similarly, $T_l$ can be calculated using the current median value multiplied by a value less than 1.0 times the value of the current median from 210. The $T_l$ can then be stored in step 225 and plotted in step 226. In a step 230, the values of the R—R intervals calculated in step 200 are compared with the values of the $T_l$ and $T_h$ thresholds calculated in step 220 to determine if the intervals are long, normal or short. R to R intervals above the $T_h$ value are considered long intervals, R to R intervals below the $T_l$ are considered short intervals, and R to R intervals between $T_l$ and $T_h$ are considered normal intervals. The long, normal, or short classifications are then stored in a step 235 and may also be plotted in a step 236.

Step 240 compiles the sequences of n, s, and L intervals in order as detected in step 230. The sequence is then evaluated in a step 250 that compares the sequences of intervals with patterns representative of known ectopic events. For example, a series of three PVC's without compensatory pauses is identified by the pattern of n, s, s, s, L; a single PVC is identified by the pattern of n, s, L, n; and a series of two PVC's with compensatory pauses is identified by the pattern of s, L, s, L. The events detected are then tabulated in a step 260. Adjustments to pacing may be made based on the number and types of events in a step 300. The tabulated report may provide the timing, number and type of events that occurred during a particular period. Further, the information on the types of ectopic beats can be stored as a step 265 and plotted as a step 266.

The total the number of occurrences of PVCs, PACs and other ectopics are stored in step 265 over a specified period, typically 24 hours. At the end of the period, each of the counters is cleared recording their outputs and sending the outputs to a trending function 270. Trending function 270 stores the trends for an extended period of days, weeks, months or years in a step 275. The trend data can be plotted in a step 276 to show the health care provider a history of the patients well being.

The particular calculations used to implement the present invention may be updated on a beat-to-beat basis by updating the dictionary in a step 251. Updating on a beat-to-beat basis allows for continuous ectopic trending and risk assessment. For example, the run of 3 PVC's 111, shown in FIG. 5, may be viewed as a potential indicator of imminent risk of sudden cardiac death. As another example, the sequence PVC, PVC, PVC, Interpolated PVC might be used as an indicator to "arm" a pacing algorithm that would head off the onset of a malignant rhythm such as indicated by 111.

The data may be displayed on a monitor such that the trending history of PVCs, and other ectopic rhythms may be represented on a daily basis and/or a weekly basis over an extended period, such as for example a year. Further, the display may include an output showing ectopy (ECT) rate and/or heart rate (HR) for a collection period. The collection period may be a day, a period weeks, a period of months or longer. The display of HR and ECT rate in PVC/5 min plotted together over the course of the previous day can assist in pinpointing the times of the day where the patient is vulnerable. Further, a chart or graph indicative of the risk factor may be displayed that goes beyond the trending function, to indicate the potential risks faced by the patient such as, for example, the occurrence of series of three PVC's as an indication an impending ventricular fibrillation.

Figure 7:
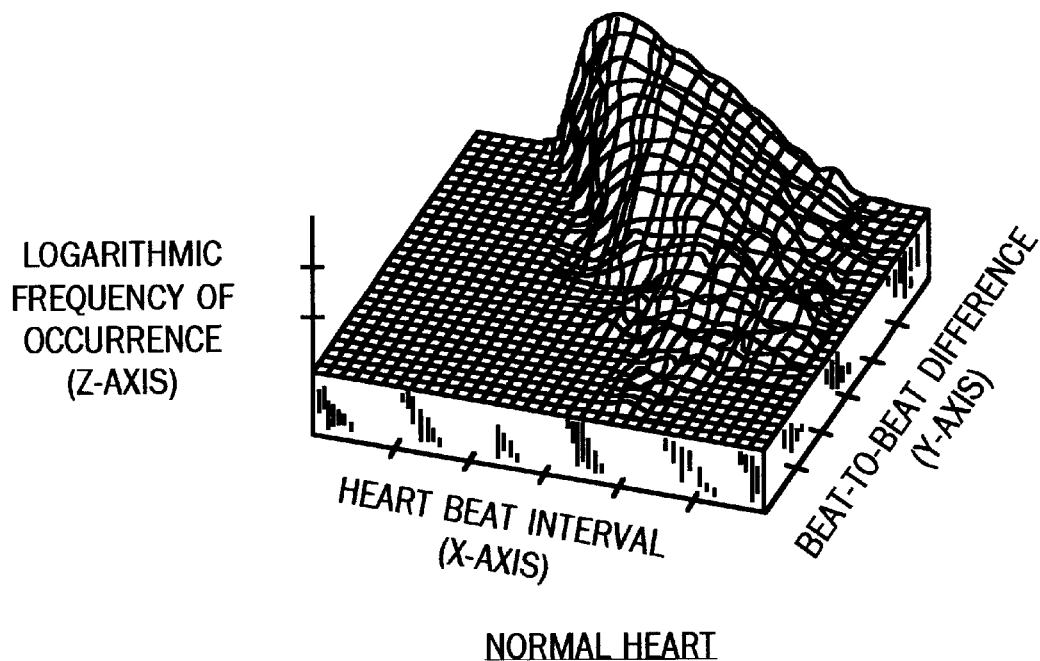
FIG. 7 shows a three-dimensional histogram of heart rate variability.
Figure 8:
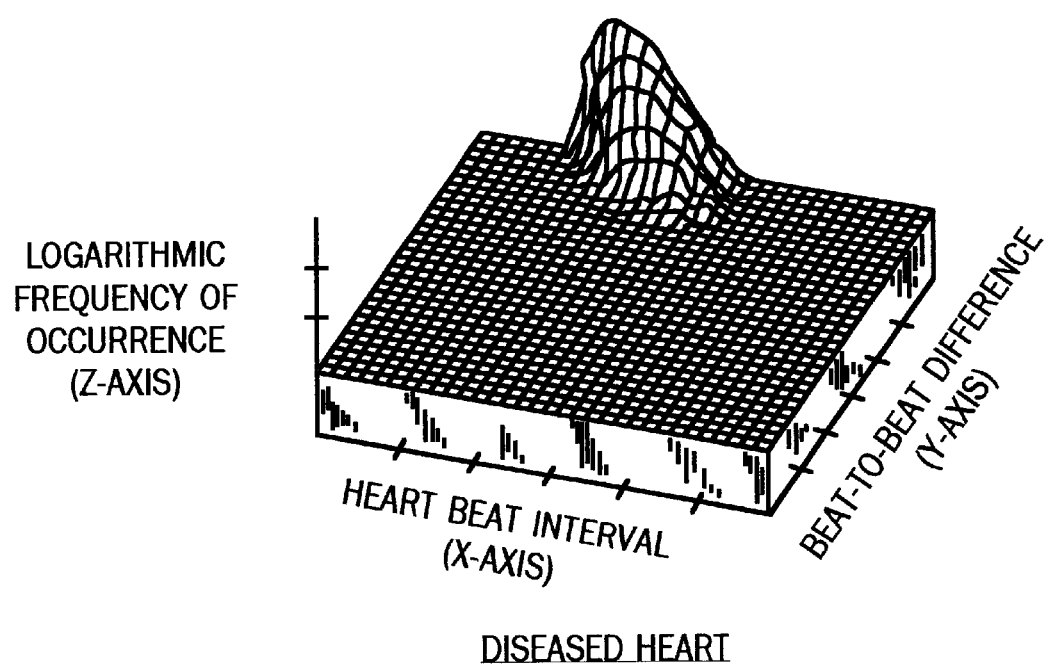
FIG. 8 shows another three-dimensional histogram of heart rate variability.

FIGS. 7 and 8 show a histogram of a healthy heart and a histogram of a diseased heart respectively, where the histograms present two-dimensionally the R to R interval activity as being a function of the current R to R interval as well as the difference in magnitude of the present and previous R to R intervals or in this case we need one extra piece of information, that is the input from the beat determination and output of the time domain log to tell us whether or not to include the beats sequences or not. The details of how to generate the histograms of FIGS. 7 and 8 are shown in the applicant's U.S. Pat. No. 5,603,331 issued Feb. 18, 1997, entitled "Data Logging System for Implantable Cardiac Device" the disclosure of which is hereby incorporated by reference. The histogram can be calculated in a step 280, shown in FIG. 6, from the R—R signal times calculated in step 200. A step 286, also shown in FIG. 6, is the plotting the histogram.

Figure 9:
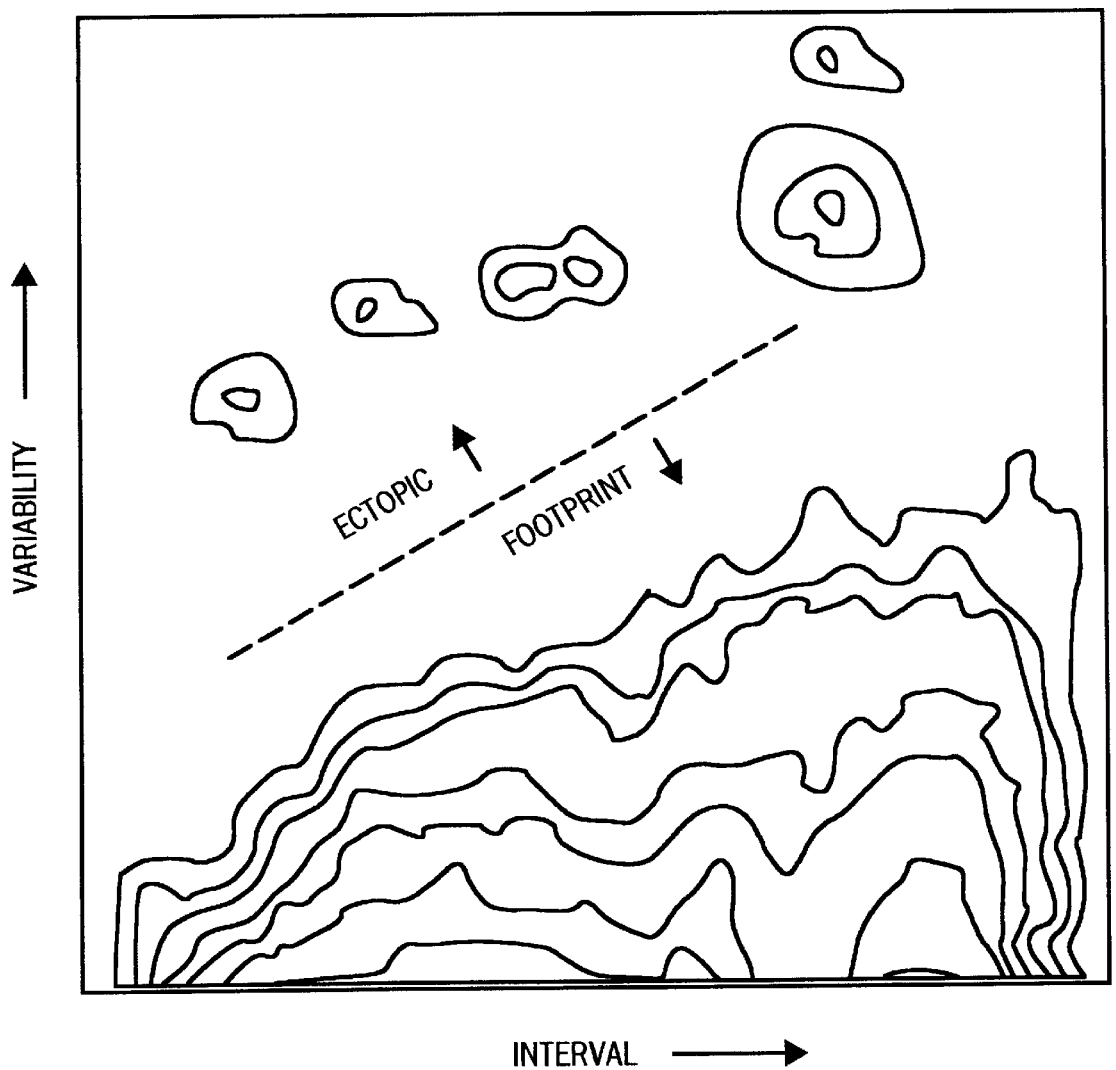
FIG. 9 shows a display of the heart beat data in the form of ectopic profiles of footprints of the heartbeats.

Using the data from the histograms on FIGS. 7 and 8 an "ectogram," "ectoprint," or ectopic footprint showing the patient's condition can be generated. A representative ectopic footprint is shown in FIG. 9. FIG. 9 on the right hand side shows the heart rate variability footprint and the ectopic footprints of the daily ectopic activity, where the horizontal axis left to right is a function of the current R to R interval and the vertical axis is an indication of the change in magnitude of the present and previous R to R intervals. In the case of an ectopic event, the R to R intervals jump away from the base line and thereby would get a distribution of ectopic activity as a function of rate. Further, microprocessor 32 may be configured to permit the review of the history of the ectopic profiles and the plotting of the history to evaluate the ectopic events over a specified period, not just the R to R intervals themselves but the beat intervals and the point the position and locations of the events labeled as ectopic. The microprocessor may be configured to allow the displaying of the sequence of ectopic events that characterize a particular ectopic island, as shown in FIG. 9. Typically, the sequence is displayed after identification of the particular island by the user. The ectopic island may be identified as a contiguous cluster of points separated by some distance from the main lobe (or sinus footprint) and other such clusters. The significance of an ectopic island is that it identifies an incidence of ectopy at a given heart rate. A family of such clusters depicts the 24-hour distribution of ectopy vs. heart rate. For example, identifying the ectopic islands above the dotted line in FIG. 9 would display the RR interval sequence in the for the time period that gave rise to the ectopic island.

In the above embodiments, the telemeter 40 connected to the microprocessor 32, both shown in FIG. 1, can send data to a receiver connected to a separate microprocessor or computer for storing data for calculating parameters and for displaying graphically the data gathered. The microprocessor 32 can then be small enough to be implantable since data accumulations are not required and large data processing requirements can be supplied from outside of the implantable device.

Many modifications and variations of the present invention are possible in light of the above teachings. It is therefore to be understood that, within the scope of the appended claims, the invention may be practiced otherwise than as specifically described.

What is claimed is:

1. A method of detecting ectopic beats, comprising:

determining time intervals between depolarizations;

calculating a trending curve for the time interval between depolarizations;

setting an upper threshold and a lower threshold relative to the trending curve;

comparing the time intervals between the depolarizations to the thresholds;

classifying the time intervals between the depolarizations relative to the thresholds as one of a long beat, a normal beat and a short beat; and recording each time interval as one of a long beat, a normal beat and a short beat.

2. A method, as in claim 1, wherein, the trending curve is calculated using a moving window median.

3. A method, as in claim 1, wherein determining time intervals between depolarizations, comprises:

sensing detecting the time of depolarizations in the heart; and calculating the time interval between the depolarizations.

4. A method, as in claim 1, wherein the beats are recorded as a sequence.

5. A method, as in claim 4, wherein the sequence of long, normal and short beats to identify types of ectopic beat activity.

6. A method, as in claim 5, further comprising counting the number of occurrences of each type of sequence that identifies a type of ectopic beat activity.

7. A method, as in claim 6, further comprising resetting the counter for the number of occurrences of each type of sequence that identifies a type of ectopic beat activity every 24 hours.

8. A method, as in claim 4, further comprising graphically displaying the number of occurrences of each type of sequence that identifies a type of ectopic beat activity for observation by a health care provider to aid in detecting the well being of the patient.

9. A method, as in claim 1, further comprising displaying the depolarization interval times for observation by a health care provider to aid in detecting the well being of the patient.

10. A method, as in claim 1, further comprising calculating a histogram having axes of, heart beat intervals, beat to beat differences, a logarithmic frequency of occurrence.

11. A method, as in claim 10, further comprising displaying a histogram based on the calculations of the histogram.

12. A method, as in claim 1, further comprising:

determining the heart rate by the detected depolarizations of the heart; and displaying one of an ectoprint and ectogram of the occurrence of ectopic beats as a function of heart rate.

13. A method of detecting ectopic beats, comprising:

a step for measuring time intervals between depolarizations;

a step for classifying the time intervals between the depolarizations one of a long beat, a normal beat and a short beat; and a step for identifying a series of beats as a pattern of long, normal and short beats to identify ectopic events.

14. A medical device, comprising:

a means for sensing the depolarizations of a heart;

a means for processing time intervals between depolarizations to detect and categorize the ectopic activity.

* * * * *